United States Patent
Tamaru et al.

(10) Patent No.: US 9,451,774 B2
(45) Date of Patent: Sep. 27, 2016

(54) PADDY RICE SEED TREATED BY HERBICIDAL COMPOSITION AND METHOD FOR CONTROLLING WEED

(71) Applicant: MITSUI CHEMICALS AGRO, INC., Chuo-ku, Tokyo (JP)

(72) Inventors: Hiroshi Tamaru, Yasu (JP); Sadafumi Koda, Yasu (JP); Kenshiro Hamamura, Ushiku (JP); Koji Handa, Kurume (JP); Hidetoshi Abe, Ushiku (JP)

(73) Assignee: MITSUI CHEMICALS AGRO, INC., Tokyo (JP)

( * ) Notice: Subject to any disclaimer, the term of this patent is extended or adjusted under 35 U.S.C. 154(b) by 0 days.

(21) Appl. No.: 14/893,009

(22) PCT Filed: May 23, 2014

(86) PCT No.: PCT/JP2014/063666
§ 371 (c)(1),
(2) Date: Nov. 20, 2015

(87) PCT Pub. No.: WO2014/189126
PCT Pub. Date: Nov. 27, 2014

(65) Prior Publication Data
US 2016/0120182 A1    May 5, 2016

(30) Foreign Application Priority Data
May 24, 2013   (JP) ................................ 2013-109566

(51) Int. Cl.
| | | |
|---|---|---|
| *A01N 43/56* | (2006.01) | |
| *A01N 25/00* | (2006.01) | |
| *A01N 25/26* | (2006.01) | |
| *A01N 37/22* | (2006.01) | |
| *A01C 1/08* | (2006.01) | |
| *A01N 41/10* | (2006.01) | |
| *A01N 43/10* | (2006.01) | |
| *A01N 43/54* | (2006.01) | |
| *A01N 43/82* | (2006.01) | |
| *A01N 47/36* | (2006.01) | |
| *A01N 47/38* | (2006.01) | |
| *A01C 1/06* | (2006.01) | |

(52) U.S. Cl.
CPC ................ *A01N 43/56* (2013.01); *A01C 1/08* (2013.01); *A01N 25/00* (2013.01); *A01N 25/26* (2013.01); *A01N 37/22* (2013.01); *A01N 41/10* (2013.01); *A01N 43/10* (2013.01); *A01N 43/54* (2013.01); *A01N 43/82* (2013.01); *A01N 47/36* (2013.01); *A01N 47/38* (2013.01)

(58) Field of Classification Search
CPC ...... A01N 43/56; A01N 37/22; A01N 41/10; A01N 43/10; A01N 43/54; A01N 43/82; A01N 47/36; A01N 47/38
See application file for complete search history.

(56) References Cited

U.S. PATENT DOCUMENTS

| | | | | |
|---|---|---|---|---|
| 6,809,065 | B2 * | 10/2004 | Hirohara ................ | A01N 43/56 504/156 |
| 7,964,531 | B2 * | 6/2011 | Tsukamoto ............ | A01N 43/58 504/137 |
| 9,107,339 | B2 * | 8/2015 | Kawano ................. | A01H 4/006 |
| 2004/0237395 | A1 | 12/2004 | Legro et al. | |
| 2005/0037925 | A1 | 2/2005 | Tsukamoto et al. | |
| 2005/0159312 | A1 | 7/2005 | Grossmann et al. | |
| 2009/0005250 | A1 | 1/2009 | Ahrens et al. | |
| 2009/0062121 | A1 * | 3/2009 | Satchivi ................. | A01N 43/40 504/105 |
| 2010/0041555 | A1 | 2/2010 | Tsukamoto et al. | |
| 2010/0323886 | A1 | 12/2010 | Voeste et al. | |

FOREIGN PATENT DOCUMENTS

| | | | | |
|---|---|---|---|---|
| JP | 8-275620 | A | 10/1996 | |
| JP | H08275620 | A | * 10/1996 | ............... A01C 1/06 |
| JP | 2005-527201 | A | 9/2005 | |
| JP | 2009/249358 | A | 10/2009 | |
| JP | 2010-513338 | A | 4/2010 | |
| JP | 2011-510957 | A | 4/2011 | |
| JP | 2012-239459 | A | 12/2012 | |
| JP | 2012239459 | A | * 12/2012 | ............... A01C 1/06 |
| WO | WO 01/13722 | A1 | 3/2001 | |
| WO | WO 03/016286 | A1 | 2/2003 | |

OTHER PUBLICATIONS

Suzuki et al., "Pyrazosulfuron-Ethyl, A New Sulfonylurea Herbicide for Paddy Rice," 1990, Pest Management in Rice, B.T. Grayson et al. (eds.), pp. 338-348.*
"Molybdenum compounds", Wikipedia [online], [retrieved Mar. 7, 2016] Retrieved from the Internet: <URL: http://en.wikipedia.org/wiki/Category:Molybdenum_compounds>.*
Suzuki et al., "Pyrazosulfuron-Ethyl, A New Sulfonylurea Herbicide for Paddy Rice," 1990; Pesticide Management in Rice, B.T. Grayson et al. (eds.), pp. 338-348.*
"Molybdenum compounds", Wikipedia [online], [retrieved Mar. 7, 2016] Retrieved from the Internet: <URL: http://en.wikiipedia.org/wiki/Category:Molybdenum_compounds>.*
International Search Report (PCT/ISA/210) mailed on Aug. 26, 2014, by the Japanese Patent Office as the International Searching Authority for International Application No. PCT/JP2014/063666.
Written Opinion (PCT/ISA/237) mailed on Aug. 26, 2014, by the Japanese Patent Office as the International Searching Authority for International Application No. PCT/JP2014/063666.

* cited by examiner

*Primary Examiner* — Jane C Oswecki
(74) *Attorney, Agent, or Firm* — Buchanan, Ingersoll & Rooney PC

(57) ABSTRACT

Disclosed are a paddy rice seed treated by a herbicidal composition and a method for controlling weed which comprises sowing the above-mentioned paddy rice seed on a surface of a soil of a paddy field.

18 Claims, No Drawings

PADDY RICE SEED TREATED BY HERBICIDAL COMPOSITION AND METHOD FOR CONTROLLING WEED

TECHNICAL FIELD

The present invention relates to paddy rice seed treated by a herbicidal composition and a method for controlling weeds which comprises sowing the paddy rice seed on a surface of a soil of a paddy field.

BACKGROUND ART

As the cultivation method of the paddy rice, a transplanting paddy rice culture which transplants raising seedling, and a direct sowing paddy rice culture which directly sows seeds have widely been known.

As the direct sowing paddy rice culture, a flooding direct sowing paddy rice culture or a dry field direct sowing paddy rice culture has been known. In addition, it has also been generally known a method in which iron powder, calcium peroxide or a molybdenum compound is coated onto a seed.

One of the great problems of the direct sowing paddy rice culture is to control weeds. The cultivation term of the direct sowing paddy rice culture is long as compared with that of the transplanting paddy rice culture, so that it is necessary to control weeds for a longer period of time. Therefore, a number of spreading a herbicide is many times which take much labor, so that labor-saving has been desired.

As a herbicide to be used in a paddy field, there have widely been known a bleaching herbicidal compound, an acetolactate synthase (hereinafter referred to as ALS) inhibitory-type herbicidal compound, a protoporphyrinogen oxidase (hereinafter referred to as PPO) inhibitory-type herbicidal compound and a very-long-chain fatty acid elongase (hereinafter referred to as VLCFAE) inhibitory-type herbicidal compound, etc.

The bleaching herbicidal compound is a well-known herbicidal compound, which kills weeds by whitening the weeds. As the bleaching herbicidal compound, for example, a pyrazole-based herbicidal compound and a triketone-based herbicidal compound have widely been known.

The pyrazole-based herbicidal compounds are, for example, pyrazolate, pyrazoxyfen and benzofenap, and are described in The Pesticide Manual 13th Edition, pp. 844-845, 848-849 and 81, respectively.

The triketone-based herbicidal compounds are, for example, mesotrione, sulcotrione and benzobicyclon, and are described in The Pesticide Manual 13th Edition, pp. 631-632, 908-909 and 80, respectively. In addition, tefuryltrione (CAS No. 473278-76-1) and bicyclopyrone (CAS No. 352010-68-5) are also the triketone-based herbicidal compounds.

Other than the pyrazole-based herbicidal compound and the triketone herbicidal compound, for example, clomazone (CAS No. 81777-89-1) or a compound 6-chloro-3-(2-cyclopropyl-6-methylphenoxy)pyridazin-4-yl morpholin-4-carboxylate (hereinafter also referred to as Compound (I)) represented by the following formula,

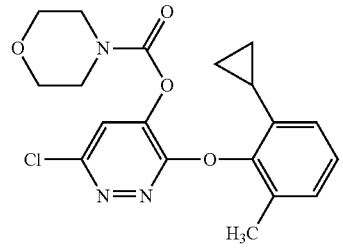

is also the bleaching herbicidal compound (Patent Document 1, Non-Patent Document 2).

The ALS inhibitory-type herbicidal compound is a well-known herbicidal compound, which kills weeds by inhibiting ALS whereby syntheses of valine, leucine and isoleucine which are essential amino acids are inhibited. As the ALS inhibitory-type herbicidal compound, for example, a sulfonylurea-based herbicidal compound, a pyrimidinylsalicylic acid-based herbicidal compound and a triazolopyrimidine-based herbicidal compound have widely been known.

The sulfonylurea-based herbicidal compounds are, for example, azimsulfuron, bensulfuron-methyl, cyclosulfamuron, halosulfuron-methyl, ethoxysulfuron, imazosulfuron, pyrazosulfuron-ethyl, chlorimuron-ethyl, cinosulfuron and metsulfuron-methyl, and are described in The Pesticide Manual 13th Edition, pp. 46-47, 73-74, 222-223, 523-524, 386-387, 560-561, 847-848, 161-162, 184-185 and 677-678, respectively. In addition, flucetosulfuron (CAS No. 412928-75-7), propylsulfuron (CAS No. 570415-88-2) and metazosulfuron (CAS No. 868680-84-6) are also the sulfonylurea-based herbicidal compounds.

The pyrimidinylsalicylic acid-based herbicidal compounds are, for example, bispyribac, pyribenzoxim, pyriftalid and pyriminobac-methyl, and are described in The Pesticide Manual 13th Edition, pp. 96-97, 852-853, 860-861 and 863-864, respectively. In addition, pyrimisulfan (CAS No. 221205-90-9) and triafamone (CAS No. 874195-61-6) are also the pyrimidinylsalicylic acid-based herbicidal compounds.

The triazolopyrimidine-based herbicidal compound is, for example, penoxsulam, and is described in The Pesticide Manual 13th Edition, pp. 753-754.

The PPO inhibitory-type herbicidal compound is a well-known herbicidal compound, which kills weeds by inhibiting PPO which causes browning symptoms. The PPO inhibitory-type herbicidal compounds are, for example, oxadiargyl, oxadiazon and pentoxazone, and are described in The Pesticide Manual 13th Edition, pp. 725-726, 727-728 and 757-758, respectively.

The VLCFAE inhibitory-type herbicidal compound is a well-known herbicidal compound, which kills weeds by inhibiting VLCFAE whereby synthesis of an aliphatic acid is inhibited. The VLCFA inhibitory-type herbicidal compounds are, for example, butachlor, pretilachlor, thenylchlor and mefenacet, and are described in The Pesticide Manual 13th Edition, pp. 118-120, 799-800, 956 and 621-622, respectively.

As a method for saving labor for spreading agricultural chemicals, there are seed treatments, and seeds to which a fungicide had been treated, seeds to which an insecticide had been treated and seeds to which a plant growth regulator had been treated have widely been known (Patent Documents 2 to 4). However, a paddy rice seed to which a herbicide had been treated has never been known. This is because different from a fungicide, an insecticide and a plant growth regulator which develop effects by absorbing these chemicals into a crop seed, whereas the herbicide an effect of which is developed by being absorbed by the weeds, by existing the herbicide used for the seed treatment at the neighbor of the seed with a high concentration, occurrence of chemical damage to the paddy rice itself becomes the problem and it is difficult to ensure a sufficient herbicidal effect at the portion apart from the seed. From such a background, a concept of treating a seed with a herbicide and controlling weeds by a seed treated by a herbicide is never thought for those skilled in the art.

Incidentally, with regard to the method for controlling weeds by plant seeds to which a herbicide has been treated, there is a description in a part of the publicly known documents, but there is neither specific description nor shown any Examples with regard to the method for controlling weeds by paddy rice seeds treated by a herbicide (Patent Documents 5 and 6).

PRIOR ART DOCUMENTS

Patent Documents

Patent Document 1: WO 03/016286A
Patent Document 2: JP 2009-249358A
Patent Document 3: WO 01/13722A
Patent Document 4: JP 2011-510957A
Patent Document 5: JP 2005-527201A
Patent Document 6: JP 2010-513338A Non-Patent Documents Non-Patent Document 1: The Pesticide Manual 13th Edition
Non-Patent Document 2: "Application file of herbicide test relating to paddy rice in 2012 (Test planning and Chemical characteristics)" (Public-interest Incorporated Foundation JAPAN ASSOCIATION FOR ADVANCEMENT OF PHYTO-REGULATORS)

SUMMARY OF THE INVENTION

Problems to be Solved by the Invention

An object of the present invention is to provide a method for controlling weeds generating in a paddy field in a labor-saving manner without providing chemical damage to paddy rice.

Means for Solving the Problems

The present inventors have intensively investigated to solve the above-mentioned problems, and as a result they found that, surprisingly, by sowing a paddy rice seed treated by a herbicidal composition onto the surface of a soil of a paddy field, and diffusing an active ingredient(s) into the paddy field through flooded water, principal weeds can be controlled, and yet, it does not cause any chemical damage against the paddy rice, so that they have accomplished the present invention.

That is, the present invention relates to the following [1] to [20].

[1]
A paddy rice seed treated by a herbicidal composition.
[2]
The paddy rice seed described in [1], wherein the herbicidal composition comprises, as an active ingredient(s),
(A1) a bleaching herbicidal compound and/or
(A2) an acetolactate synthase inhibitory-type herbicidal compound, or a salt thereof.
[3]
The paddy rice seed described in [2], wherein the component (A1) is a pyrazole-based herbicidal compound, a triketone-based herbicidal compound and/or 6-chloro-3-(2-cyclopropyl-6-methylphenoxy)pyridazin-4-yl morpholin-4-carboxylate
or a salt thereof.
[4]
The paddy rice seed described in [2] or [3], wherein the component (A2) is a sulfonylurea-based herbicidal compound and/or a pyrimidinylsalicylic acid-based herbicidal compound
or a salt thereof.
[5]
The paddy rice seed described in any one of [2] to [4], wherein the component (A1) is pyrazolate and/or 6-chloro-3-(2-cyclopropyl-6-methylphenoxy)pyridazin-4-yl morpholin-4-carboxylate. [6]
The paddy rice seed described in any one of [2] to [5], wherein the component (A1) is pyrazolate.
[7]
The paddy rice seed described in any one of [1] to [6], wherein the seed is treated by the herbicidal composition and coated by iron powder, calcium peroxide and/or a molybdenum compound.
[8]
The paddy rice seed described in any one of [1] to [6], wherein the seed is treated by the herbicidal composition and coated by iron powder.
[9]
The paddy rice seed described in any one of [1] to [8], wherein an amount of an active ingredient of the herbicidal composition to be formulated based on 1 kg of the paddy rice seed is 0.01 g to 3,000 g.
[10]
The paddy rice seed described in any one of [1] to [8], wherein an amount of an active ingredient of the herbicidal composition to be formulated based on 1 kg of the paddy rice seed is 0.1 g to 1,000 g.
[11]
A method for controlling weed which comprises sowing paddy rice seed treated by a herbicidal composition on a surface of a soil of a paddy field.
[12]
The method for controlling weed described in [11], wherein the herbicidal composition comprises, as an active ingredient(s),
(A1) a bleaching herbicidal compound and/or
(A2) an acetolactate synthase inhibitory-type herbicidal compound,
or a salt thereof.
[13]
The method for controlling weed described in [12], wherein the component (A1) is a pyrazole-based herbicidal compound, a triketone-based herbicidal compound and/or 6-chloro-3-(2-cyclopropyl-6-methylphenoxy)pyridazin-4-yl morpholin-4-carboxylate or a salt thereof. [14]

The method for controlling weed described in [12] or [13], wherein the component (A2) is a sulfonylurea-based herbicidal compound and/or a pyrimidinylsalicylic acid-based herbicidal compound or a salt thereof. [15]

The method for controlling weed described in any one of [12] to [14], wherein the component (A1) is pyrazolate and/or 6-chloro-3-(2-cyclopropyl-6-methylphenoxy)-pyridazin-4-yl morpholin-4-carboxylate.

[16]

The method for controlling weed described in any one of [12] to [15], wherein the component (A1) is pyrazolate.

[17]

The method for controlling weed described in any one of [11] to [16], wherein the paddy rice seed treated by the herbicidal composition and coated by iron powder, calcium peroxide and/or a molybdenum compound is sown on a surface of a soil of a paddy field.

[18]

The method for controlling weed described in any one of [11] to [16], wherein the paddy rice seed treated by the herbicidal composition and coated by iron powder is sown on a surface of a soil of a paddy field.

[19]

The method for controlling weed described in any one of [11] to [18], wherein an amount of an active ingredient of the herbicidal composition to be formulated based on 1 kg of the paddy rice seed is 0.01 g to 3,000 g.

[20]

The method for controlling weed described in any one of [11] to [18], wherein an amount of an active ingredient of the herbicidal composition to be formulated based on 1 kg of the paddy rice seed is 0.1 g to 1,000 g.

Effect of the Invention

A paddy rice seed and a method for controlling weed of the present invention prevent various kinds of weeds which causes problems in a paddy field including, for example, gramineous weeds such as *Echinochloa oryzicola*, etc.; Scrophulariaceae weeds such as *Lindernia procumbens, Dopatrium junceum*, etc.; Pontederiaceae weeds such as *Monochoria vaginalis, Monochoria korsakowii*, etc.; Cyperaceae weeds such as *Cyperus difformis, Scirpus juncoides* Roxb., *Eleocharis acicularis*, etc.; and/or Alismataceae weeds such as *Sagittaria pygmaea, Sagittaria trifolia, Alisma canaliculatum*, etc., and show no chemical damage which causes problems against the paddy rice. In addition, the weeds can be controlled simultaneously with sowing, so that spreading of the herbicide thereafter can be labor-saved.

Accordingly, the paddy rice seed and the method for controlling weed of the present invention can reduce labor necessary for a weed controlling operation.

EMBODIMENTS TO CARRY OUT THE INVENTION

Each term used in the claims and the specification of the present application is based on the definition generally used in the field of chemistry otherwise specifically mentioned.

The paddy rice seed treated by the herbicidal composition of the present invention is an optional paddy rice seed to which the herbicidal composition has been treated, by the seed treatment techniques known in this field of the art, for example, a seed dust coating method, a seed coating method, a seed scatter dusting method, a seed dipping method and a seed pelleting method, etc.

In the present invention, an optional herbicidal composition can be used for an optional variety of a paddy rice seed. However, it is preferred to use a variety of a paddy rice seed having no sensitivity to the herbicidal composition. In the present invention, "having no sensitivity" means that no chemical damage is generated in the chemical treatment at the flooding condition in the usual transplantation cultivation.

It is clear for those skilled in the art that which variety of a paddy rice seed has no sensitivity to a herbicidal composition, and as a variety of the paddy rice seed having no sensitivity to the herbicidal composition, there may be mentioned, for example, Koshihikari, Hinohikari, Hitomebore, Akitakomachi, Kinuhikari, Nanatsuboshi, Haenuki, Kirara 397, Masshigura, Tsugaru Roman, Nipponbare, etc. Also, a paddy rice seed having no sensitivity to the PPO inhibitory-type herbicidal compound or the VLCFAE inhibitory-type herbicidal compound, for example, Koshihikari, Hinohikari, Hitomebore, Akitakomachi and Kinuhikari may be preferably used.

On the other hand, as a variety of the paddy rice seed showing sensitivity to the herbicidal composition, there may be mentioned, for example, Habataki, Takanari, Momiroman, Mizuhochikara, Ruriaoba and Odorokimochi, which show sensitivity to mesotrione or benzobicyclon. With regard to the paddy rice seeds showing sensitivity to these herbicidal compositions, there is described in, for example, "Japanese Journal of Crop Science 79 (Extra 1)".

As the paddy rice seed to be used in the present invention, a seed which is in the state of capable of sowing may be used, and a seed which has already germinated may be also used.

Also, as the paddy rice seed to be used in the present invention, a coated seed may be used. The coating agent to be used for the paddy rice seed of the present invention is, for example, iron powder, calcium peroxide or a molybdenum compound, suitably iron powder.

The paddy rice seed of the present invention is treated by a herbicidal composition containing an optional herbicidal compound generally used in a paddy field as an active ingredient(s). As such a herbicidal compound, there may be mentioned the bleaching herbicidal compound and the ALS inhibitory-type herbicidal compound, etc., as exemplified above. The paddy rice seed of the present invention is preferably treated by a herbicidal composition an active ingredient(s) of which is the bleaching herbicidal compound and/or the ALS inhibitory-type herbicidal compound, or a salt thereof.

As the bleaching herbicidal compound in the present invention, there may be mentioned, for example, a pyrazole-based herbicidally active compound, a triketone-based herbicidally active compound, clomazone, 6-chloro-3-(2-cyclopropyl-6-methylphenoxy)pyridazin-4-yl morpholin-4-carboxylate, etc.

As the pyrazole-based herbicidally active compound, there may be mentioned, for example, pyrazolate, pyrazoxyfen, benzofenap, etc. These compounds belong to Group F2 of HRAC classification system.

As the triketone-based herbicidally active compound, there may be mentioned, for example, mesotrione, sulcotrione, benzobicyclon, tefuryltrione, bicyclopyrone, etc. These compounds belong to Group F2 of HRAC classification system.

Clomazone belongs to Group F4 of HRAC classification system.

As the ALS inhibitory-type herbicidal compound, there may be mentioned, a sulfonylurea-based herbicidal compound, a pyrimidinylsalicylic acid-based herbicidal compound, etc. These compounds belong to Group B of HRAC classification system.

As the sulfonylurea-based herbicidal compound, there may be mentioned, for example, azimsulfuron, bensulfuron-methyl, cyclosulfamuron, halosulfuron-methyl, ethoxysulfuron, imazosulfuron, pyrazosulfuron-ethyl, chlorimuron-ethyl, cinosulfuron, metsulfuron-methyl, flucetosulfuron, propylsulfuron, metazosulfuron, etc.

As the pyrimidinylsalicylic acid-based herbicidal compound, there may be mentioned, for example, bispyribac, pyribenzoxim, pyriftalid, pyriminobac-methyl, pyrimisulfan, triafamone, etc.

With regard to the predetermined mechanism of action and classification of these herbicidal compound groups, there are described in, for example, "Application file of herbicide test relating to paddy rice in 2012 (Test planning and Chemical characteristics)" (Public-interest Incorporated Foundation JAPAN ASSOCIATION FOR ADVANCEMENT OF PHYTO-REGULATORS) and "HRAC (Herbicide Resistance Action Committee), According to HRAC classification on mode of action".

The herbicidal composition to be used in the present invention may contain a stock material of the herbicidal compound alone, or, if necessary, by formulating a carrier and the other auxiliary agents, it may be used by forming a preparation with the preparation form which can be generally used as a seed treating agent, for example, a solid preparation such as powder, wettable powder, a granular hydrating agent, etc., and a liquid preparation such as a liquid agent, an emulsion, a flowable and an emulsion preparation, etc.

The carrier herein mentioned means a synthetic or natural inorganic or organic substance to be mixed with the herbicidal composition for the purpose of aiding reachability of the herbicidal compound to the plant, or making storage, transportation or handling easy.

A concentration of the herbicidal compound in the herbicidal composition may be optionally determined depending on a kind of the herbicidal compound and a preparation form to be used.

The paddy rice seed of the present invention can be obtained by treating the above-mentioned optional paddy rice seed with the above-mentioned herbicidal composition by the seed treatment techniques, for example, a seed dust coating method, a seed coating method, a seed scatter dusting method, a seed dipping method and a seed pelleting method, etc. The "dust coating method" means a method in which a powder material or wettable powder is powdered on the seeds, and is, in principle, a treatment method in which the seeds and the powder material are charged in a vessel and stirred to attach the powder material onto the surface of the seeds. In place of the powder material in the dust coating method, a chemical liquid or a slurry may be used.

For the treatment, a treatment amount of the herbicidal composition may be optionally determined depending on a kind of the herbicidal compound and the preparation form of the herbicidal composition. For example, based on 1 kg of the seeds, as the active component of the herbicidal compound, the treatment amount of the herbicidal composition can be determined so that it is treated with 0.01 g to 3,000 g, suitably 0.1 g to 1,000 g.

When the paddy rice seed is treated by the coating agent such as iron powder, calcium peroxide or a molybdenum compound, etc., as mentioned above, the coating agent and the herbicidal composition may be treated simultaneously, or one of which may be primarily treated, and then, the other may be treated thereafter. The order of the treatment is optional. Or else, the above-mentioned coating agent is formulated to the herbicidal composition, and then, the seed may be treated.

In the present invention, the seed treatment by the herbicidal composition is carried out before sowing the paddy rice.

The paddy rice seed of the present invention may be treated by the herbicidal composition solely, or may be treated simultaneously with a fungicide, an insecticide, an acaricide, a nematicide, a phytotoxicity-reducing agent or a plant growth regulator. As the fungicide used for the simultaneous treatment, there may be mentioned, for example, a strobilurin-based compound, an anilinopyrimidine-based compound, an azole-based compound, a dithiocarbamate-based compound, a phenylcarbamate-based compound, an organic chlorine-based compound, a benzimidazole-based compound, a phenylamide-based compound, a sulfenic acid-based compound, a copper-based compound, an isoxazole-based compound, an organic phosphorus-based compound, an N-halogenothioalkyl-based compound, a carboxyanilide-based compound, a morpholine-based compound, an organic tin-based compound and/or a cyanopyrrole-based compound, and as an insecticide, an acaricide or a nematicide, there may be mentioned, for example, a pyrethroid-based compound, an organic phosphorus-based compound, an oxime-carbamate-based compound, a carbamate-based compound, a neonicotinoid-based compound, a diacylhydrazine-based compound, a benzoylurea-based compound, a juvenile hormone-based compound, a cyclodiene organic chlorine-based compound, a 2-dimethylaminopropane-1,3-dithiol-based compound, an amidine-based compound, a phenylpyrazole-based compound, an organic tin-based compound, an METI-based compound, a benzilate-based compound, an allylpyrrol-based compound, a dinitrophenol-based compound, an anthranyl-diamide-based compound, an oxadiazine-based compound, a semicarbazone-based compound, a tetronic acid-based compound, a carbamoyl-triazole-based compound and/or a tetrazine-based compound, but the present invention is not limited by these.

More specifically, there may be mentioned, for example, the following compounds:

a strobilurin-based compound such as azoxystrobin, kresoxym-methyl, trifloxystrobin, metominostrobin, orysastrobin, pyraclostrobin, picoxystrobin, etc., an anilinopyrimidine-based compound such as mepanipyrim, pyrimethanil, cyprodinil, etc., an azole-based compound such as triadimefon, bitertanol, triflumizole, metoconazole, propiconazole, penconazole, flusilazole, myclobutanil, cyproconazole, tebuconazole, hexaconazole, prochloraz, simeconazole, fenarimol, imazalil, epoxiconazole, prothioconazole, ipconazole, pefurazoate, etc., a quinoxaline-based compound such as quinomethionate, etc., a dithiocarbamate-based compound such as maneb, zineb, mancozeb, polycarbamate, propineb, thiram, etc., a phenylcarbamate-based compound such as diethofencarb, etc., an organic chlorine-based compound such as chlorothalonil, quintozene, etc., a benzimidazole-based compound such as benomyl, thiophanate-methyl, carbendazole, etc., a phenylamide-based compound such as metalaxyl, metalaxyl-M, oxadixyl, ofurase, benalaxyl, furalaxyl, cyprofuram, etc., a sulfenic acid-based compound such as dichlofluanid, etc., a copper-based compound such as cupric hydroxide (copper hydroxide), copper quinolate (oxine-copper), etc., an isoxazole-based compound such as hydroxyisoxazole, etc., an organic phosphorus-based compound such as fosetyl-aluminium, tolclofos-methyl, etc., an N-halogenothioalkyl-based compound such as captan, captafol, folpet, etc., a dicarboxyimide-based compound such as procymidone, iprodione, vinclozolin, etc., a carboxyanilide-based compound such as flutolanil, mepronil, furametpyr, thifluzamide, boscalid, penthiopyrad, isofetamid, fluopyram, sedaxane, bixafen, penflufen, fluxapyroxad, isopyrazam, benzovindiflupyr, etc., a morpholine-based compound such as fenpropimorph, dimethomorph, etc., an organic tin-based compound such as triphenyl tin hydroxide (fenthin hydroxide), triphenyl tin acetate (fentin acetate), etc., a cyanopyrrole-based compound such as fludioxonil, fenpiclonil, etc., and other fungicides such as tricyclazole, pyroquilon, carpropamid, diclocymet, fenoxanil, fthalide, fluazinam, cymoxanil, triforine, pyrifenox, fenpropidin, pencycuron, ferimzone, cyazofamid, amisulbrom, iprovalicarb, benthiavalicarb-isopropyl, iminoctadine-albesilate, cyflufenamid, kasugamycin, validamycin, isoprothiolane, streptomycin, oxolinic-acid, tebufloquin, probenazole, tiadinil, isotianil, tolprocarb, MIF-1002, etc., a pyrethroid-based compound such as acrinathrin, allethrin [(1R)-isomer], bifenthrin, bioallethrin, bioallethrin S-cyclopentenyl isomer, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, methothrin, metofluthrin, permethrin, phenothrin [(1R)-trans-isomer], prallethrin, resmethrin, RU15525 (kadethrin), silafluofen, tefluthrin, tetramethrin, tetramethrin [(1R)-isomer], tralomethrin, transfluthrin, ZXI8901, biopermethrin, furamethrin, profluthrin, flubrocythrinate, dimefluthrin, etc., and various isomers thereof, an organic phosphorus-based compound such as acephate, azamethiphos, azinphos-methyl, azinphos-ethyl, cadusafos, chlorethoxyfos, chlorfenvinphos, chlormephos, chlorpyrifos, chlorpyrifos-methyl, coumaphos, CYAP (cyanophos), demeton-S-methyl, diazinon, ECP (dichlofenthion), DDVP (dichlorvos), dicrotophos, dimethoate, dimethylvinphos, disulfoton (ethylthiometon), EPN (O-ethyl O-4-nitrophenyl phenylphosphonothioate), ethion, ethoprophos, Famphur, fenamiphos, MEP (fenitrothion), MPP (fenthion), fosthiazate, heptenophos, isofenphos-methyl, Isocarbophos (isopropyl O-(methoxyaminothio=phosphoryl)salicylate), isoxathion, malathion, mecarbam, methamidophos, DMTP (methidathion), mevinphos, monocrotophos, BRP (naled), omethoate, oxydemeton-methyl, parathion, parathion-methyl, PAP (phenthoate), phorate, phosalone, phosmet, phosphamidon, phoxim, pirimiphos-methyl, profenofos, propetamphos, prothiofos, pyraclofos, pyridaphenthion, quinalphos, Sulfotep, tebupirimfos, temephos, terbufos, thiometon, triazophos, DEP (trichlorfon), vamidothion, Bayer 22/190 (chlorothion), bromfenvinfos, bromophos, bromophos-ethyl, butathiofos, carbophenothion, Chlorphoxim, sulprofos, diamidafos, CVMP (tetrachlorvinphos), propaphos, mesulfenfos, dioxabenzofos (salithion), etrimfos, oxydeprofos, formothion, fensulfothion, isazofos, imicyafos (AKD3088), isamidofos, thionazin, fosthietan, etc., an oxime-carbamate-based compound such as phosphocarb, alanycarb, butocarboxim, butoxycarboxim, thiodicarb, Thiofanox, etc., a carbamate-based compound such as aldicarb, bendiocarb, benfuracarb, NAC (carbaryl), carbofuran, carbosulfan, ethiofencarb, BPMC (fenobucarb), Formetanate, furathiocarb, MIPC (isoprocarb), methiocarb, methomyl, oxamyl, pirimicarb, PHC (propoxur), trimethacarb, XMC (3,5-xylyl methylcarbamate), allyxycarb, aldoxycarb, bufencarb, butacarb, carbanolate, MTMC (metolcarb), MPMC (xylylcarb), fenothiocarb, bendiocarb, etc., a neonicotinoid-based compound such as acetamiprid, clothianidin, dinotefuran, imidacloprid, nitenpyram, thiacloprid, thiamethoxam, etc., a diacylhydrazine-based compound such as chromafenozide, halofenozide, methoxyfenozide, tebufenozide, etc., a benzoylurea-based compound such as bistrifluron, chlorfluazuron, diflubenzuron, flucycloxuron, flufenoxuron, hexaflumuron, lufenuron, novaluron, noviflumuron, teflubenzuron, triflumuron, etc., a juvenile hormone-based compound such as fenoxycarb, hydroprene, kinoprene, methoprene, pyriproxyfen, etc., a cyclodiene organic chlorine-based compound such as chlordane, endosulfan, lindane (gamma-HCH), dienochlor, etc., a 2-dimethylaminopropane-1,3-dithiol-based compound such as Cartap hydrochloride, thiocyclam, etc., an amidine-based compound such as amitraz, etc., a phenylpyrazole-based compound such as ethiprole, fipronil, acetoprole, etc., an organic tin-based compound such as azocyclotin, cyhexatin, hexakis(2-methyl-2-phenylpropyl)distannoxane (fenbutatin oxide), etc., an METI-based compound such as fenazaquin, fenpyroximate, pyridaben, pyrimidifen, tebufenpyrad, tolfenpyrad, etc., a benzilate-based compound such as bromopropylate, etc., an allylpyrrol-based compound such as chlorfenapyr, etc., a dinitrophenol-based compound such as DNOC, binapacryl, etc., an anthranyl-diamide-based compound such as chlorantraniliprole, cyantraniliprole, etc., an oxadiazine-based compound such as indoxacarb, etc., a semicarbazone-based compound such as metaflumizone, etc., a tetronic acid-based compound such as spirodiclofen, spiromesifen, spirotetramat, etc., a carbamoyltriazole-based compound such as triazamate, etc., a tetrazine-based compound such as diflovidazin, etc., an insecticide, an acaricide and a nematicide such as abamectin, emamectin benzoate, milbemectin, lepimectin, acequinocyl, azadirachtin, bensultap, Benzoximate, bifenazate, buprofezin, CGA-50439, chinomethionat, clofentezine, cryolite, cyromazine, dazomet, DCIP, DDT, diafenthiuron, D-D (1,3-Dichloropropene), dicofol, dicyclanil, dinobuton, dinocap, ENT 8184, etoxazole, flonicamid, fluacrypyrim, flubendiamide, GY-81 (peroxocarbonate), hexythiazox, hydramethylnon, methyl iodide, karanjin, MB-599 (verbutin), metam, methoxychlor, methyl isothiocyanate, pentachlorophenol, phosphine, piperonyl butoxide, polynactin complex (polynactins), BPPS (propargite), pymetrozine, pyrethrins, pyridalyl, rotenone, 5421 (bis(2,3,3,3-tetrachloropropyl) ether), sabadilla, spinosad, spinetoram, sulcofuron salt (sulcofuron-sodium), sulfluramid, tetradifon, thiosultap, Tribufos, aldrin, amidithion, amidothioate, aminocarb, amiton, aramite, athidathion, azothoate, barium polysulphide, Bayer 22408, Bayer 32394, benclothiaz, 5-(1,3-benzodioxo1-5-yl)-3-hexylcyclohexa-2-enone, 1,1-bis(4-chlorophenyl)-2-ethoxyethanol, butonate, butopyronoxyl, 2-(2-butoxyethoxy)ethyl thiocyanate, camphechlor, chlorbenside, chlordecone, chlordimeform, chlorfenethol, chlorfenson, isoprothiolane, fluazuron, metaldehyde, phenisobromolate, fluazinam, bialaphos, benomyl, levamisole hydrochloride (levamisol), pyrifluquinazon, cyflumetofen, amidoflumet, IKA-2005, cyenopyrafen (NC512), sulfoxaflor, pyrafluprole (V3039), pyriprole (V3086), tralopyril, flupyrazofos, diofenolan, chlorobenzilate, flufenzine, benzomate, flufenerim, Tripropyl isocyanurate (TPIC), albendazole, oxibendazole, fenbendazole, metam-sodium, 1,3-dichloropropene, flupyradifurone, afidopyropen, flometoquin, pyflubumide, fluensulfone, IKI-3106, etc.

As the phytotoxicity-reducing agent to be used for the simultaneous treatment, there may be mentioned, for example, benoxacor, furilazole, dichlormid, dicyclonon, DKA-24 (N1,N2-diallyl-N2-dichloroacetylglycineamide), AD-67 (4-dichloroacetyl-1-oxa-4-azaspiro[4.5]decane), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazolidine), cloquintocet-mexyl, naphthalic anhydride (1,8-Naphthalic Anhydride), mefenpyr-diethyl, mefenpyr, mefenpyr-ethyl, fenchlorazole-ethyl, fenclorim, MG-191 (2-dichloromethyl-2-methyl-1,3-dioxane), cyometrinil, flurazole, fluxofenim, isoxadifen, isoxadifen-ethyl, dymron (daimuron), oxabetrinil, cyprosulfamide, lower alkyl-substituted benzoic acid, cumyluron and/or TI-35 (1-dichloroacetylazepane), but the present invention is not limited by these.

The paddy rice seed treated by the herbicidal composition of the present invention may be sown on the surface of the paddy field or in the soil, under the flooding condition, or may be sown under the water drainage condition and then flooded. As the direct sowing system under flooding, there is a drilling system with a mechanical type or an air pressure injection type, a spreading system by a knapsack power applicator or a radio controlled helicopter, or a hill sowing system using seed-shooting seeder of rice combined with a paddy harrow, etc. On the other hand, after cultivating the soil in a paddy state, water is once drained and sowing is carried out, the field may be again flooded after growing a young rice plant with a certain extent. The paddy rice seed according to the present invention is preferably directly sown onto the surface of the soil of the paddy field in the viewpoint of controlling chemical damage by the herbicidal composition to be used for the treatment.

In other aspect of the present invention, a paddy rice seed treated by a herbicidal composition suitable for the variety of the paddy rice to be cultivated can be produced. A method for producing such a paddy rice seed comprises preparing one or a plural number of herbicidal compositions, comparing preventive effects of the herbicidal composition(s) exerted on growth of the principal weeds and the variety of the paddy rice to be cultivated, selecting the herbicidal composition(s) which show(s) sufficient effects on the principal weeds, and show(s) no preventive effects or show(s) a relatively weak preventive effects against growth of the above-mentioned variety of the paddy rice, and treating seeds of the above-mentioned variety of the paddy rice with the selected herbicidal composition(s).

The herbicidal composition to be used for the above-mentioned preparation method preferably contains, as an active ingredient(s), the above-mentioned (A1) bleaching herbicidal compound and/or (A2) acetolactate synthase inhibitory-type herbicidal compound or a salt thereof. On the other hand, with regard to a variety of a specific paddy rice having a relatively high sensitivity to the herbicidal composition, a paddy rice seed treated by the herbicidal composition can be produced by selecting an active ingredient having a low growth controlling effect by the above-mentioned method and treating the seed. Further, the growth controlling effect to the cultivation variety would be suppressed as little as possible by adjusting a content of the active ingredient(s), by devising the treatment method by the herbicidal composition, or by mixing the above-mentioned phytotoxicity-reducing agent.

EXAMPLES

In the following, Preparation examples of the herbicidal compositions to be used in the present invention and Test examples for controlling weeds are shown and specifically explained, but the present invention is not limited by these. Incidentally, in the following Preparation examples, "%" means % by mass.

Preparation Example 1

Pyrazolate (10 parts by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 64.5 parts by mass) were thoroughly mixed and pulverized to obtain a wettable powder of pyrazolate (10%).

Preparation Example 2

Compound (I) (5 parts by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 69.5 parts by mass) were thoroughly mixed and pulverized to obtain a wettable powder of Compound (I) (5%).

Preparation Example 3

Sulcotrione (0.1 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.4 parts by mass) were thoroughly mixed and pulverized to obtain a wettable powder of sulcotrione (0.1%).

Preparation Example 4

Imazosulfuron (0.1 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.4 parts by mass) were thoroughly mixed and pulverized to obtain a wettable powder of imazosulfuron (0.1%).

Preparation Example 5

Pyrimisulfan (0.1 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.4 parts by mass) were thoroughly mixed and pulverized to obtain a wettable powder of pyrimisulfan (0.1%).

Preparation Example 6

Pyriminobac-methyl (0.1 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.4 parts by mass) were thoroughly mixed and pulverized to obtain a wettable powder of pyriminobac-methyl (0.1%).

Preparation Example 7

Thenylchlor (0.1 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.4 parts by mass) were thoroughly mixed and pulverized to obtain a wettable powder of thenylchlor (0.1%).

Preparation Example 8

Oxadiargyl (0.1 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.4 parts by mass) were thoroughly mixed and pulverized to obtain a wettable powder of oxadiargyl (0.1%).

Preparation Example 9

Butachlor (0.1 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.4 parts by mass) were thoroughly mixed and pulverized to obtain a wettable powder of butachlor (0.1%).

Preparation Example 10

Dinotefuran (0.5 part by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 74.0 parts by mass) were thoroughly mixed and pulverized to obtain a wettable powder of dinotefuran (0.5%).

Preparation Example 11

Dymron (5 parts by mass), Carplex #80D™ (available from Shionogi & Co., Ltd., 10 parts by mass), Newcol 291PG™ (dioctyl sulfosuccinate sodium salt, available from Nippon Nyukazai Co., Ltd., 0.5 part by mass), NEOGEN™ Powder (available from DKS Co., Ltd., 5 parts by mass), Radiolight #200™ (available from Showa Chemical Industry Co., Ltd., 10 parts by mass) and H fine powder (available from Keiwa Rozai Co., Ltd., 69.5 parts by mass) were thoroughly mixed and pulverized to obtain a wettable powder of dymron (5%).

Test Example 1

In 100 cm$^2$ of a pot was filled a paddy field soil, and after paddling, seeds of *Monochoria vaginalis* and *Lindernia procumbens* were sown and mixed into the surface layer of the soil. Paddy rice seeds (variety: Nipponbare) sprouted into a pigeon breast shape were dust-coated with a predetermined amount of wettable powder each prepared according to Preparation examples 1, 2 and 7, and were sown onto the surface of the soil or into the soil (depth: 1 cm) at an amount of 10 grains/pot. After the sowing, water was introduced quietly and flooded up to 1 cm. After 30 days from the sowing, a growth inhibition rate was judged according to the following judgement criteria. The results are shown in Table 1.

Judgement Criteria

0: Growth inhibition rate of 0 to 9%
1: Growth inhibition rate of 10 to 18%
2: Growth inhibition rate of 19 to 27%
3: Growth inhibition rate of 28 to 36%

-continued

4: Growth inhibition rate of 37 to 45%
5: Growth inhibition rate of 46 to 54%
6: Growth inhibition rate of 55 to 63%
7: Growth inhibition rate of 64 to 72%
8: Growth inhibition rate of 73 to 81%
9: Growth inhibition rate of 82 to 90%
10: Growth inhibition rate of 91 to 100%

Test Example 2

In 100 cm² of a pot was filled a paddy field soil, and after paddling, seeds of *Monochoria vaginalis* and *Lindernia procumbens* were sown and mixed into the surface layer of the soil. Also, paddy rice seeds (variety: Koshihikari) dipped in 20° C. of water for 2 days were dust-coated with a mixture of iron powder and calcined gypsum (a mixing ratio of 10:1) with an amount of 100 g per 1 kg of the seeds (dried unhulled rice) to prepare iron powder-coated seeds. The iron powder-coated paddy rice seeds were dust-coated with a predetermined amount of wettable powder each prepared according to Preparation examples 1 to 4, and were sown onto the surface of the soil under the flooding condition with the water depth of 1 cm at an amount of 10 grains/pot. After 21 days from the sowing, a growth inhibition rate was judged according to the above-mentioned judgement criteria. The results are shown in Table 2.

TABLE 1

| Compound | Dosage (a.i. g) per 1 kg of seeds | Sowing method of paddy rice | *Monochoria vaginalis* | *Lindernia procumbens* | Paddy rice |
| --- | --- | --- | --- | --- | --- |
| Pyrazolate | 150 | Surface | 10 | 10 | 0 |
| Compound (I) | 37.5 | sowing | 10 | 10 | 0 |
| Thenylchlor | 0.63 | | 7 | 9 | 6 |
| Pyrazolate | 150 | Sowing into | 8 | 7 | 3 |
| Compound (I) | 37.5 | soil | 9 | 8 | 5 |
| Thenylchlor | 0.63 | | 6 | 8 | 9 |

TABLE 2

| Compound | Dosage (a.i. g) per 1 kg of seeds | Sowing method of paddy rice | *Monochoria vaginalis* | *Lindernia procumbens* | Paddy rice |
| --- | --- | --- | --- | --- | --- |
| Pyrazolate | 150 | Surface | 10 | 10 | 0 |
| Compound (I) | 38 | sowing | 10 | 10 | 0 |
| Sulcotrione | 1.0 | | 10 | 10 | 0 |
| Imazosulfuron | 1.0 | | 10 | 10 | 0 |

Test Example 3

In 100 cm² of a pot was filled a paddy field soil, and after paddling, seeds of *Echinochloa oryzicola* and *Scirpus juncoides* Roxb. were sown and mixed into the surface layer of the soil. Also, paddy rice seeds (variety: Koshihikari) dipped in 20° C. of water for 2 days were dust-coated with a mixture of iron powder and calcined gypsum (a mixing ratio of 10:1) with an amount of 100 g per 1 kg of the seeds (dried unhulled rice) to prepare iron powder-coated seeds. The iron powder-coated paddy rice seeds were dust-coated with a predetermined amount of wettable powder each prepared according to Preparation examples 5 and 6, and were sown onto the surface of the soil under the flooding condition with the water depth of 1 cm at an amount of 10 grains/pot. After 22 days from the sowing, a growth inhibition rate was judged according to the above-mentioned judgement criteria. The results are shown in Table

TABLE 3

| Compound | Dosage (a.i. g) per 1 kg of seeds | Sowing method of paddy rice | *Echinochloa oryzicola* | *Scirpus juncoides* Roxb. | Paddy rice |
| --- | --- | --- | --- | --- | --- |
| Pyrimisulfan | 0.5 | Surface | 10 | 10 | 0 |
| Pyriminobac-methyl | 1.5 | sowing | 10 | 0 | 0 |

Test Example 4

In 800 cm² of a pot was filled a paddy field soil, and after paddling, seeds of *Monochoria vaginalis* and *Lindernia procumbens* were sown and mixed into the surface layer of the soil. Paddy rice seeds (variety: Nipponbare) sprouted into a pigeon breast shape were dust-coated with a predetermined amount of wettable powder prepared according to Preparation example 1, and were sown onto the surface of the soil under the flooding condition with the water depth of 1 cm at an amount of 20 grains/pot.

After 21 days from the sowing, a growth inhibition rate was judged according to the following judgement criteria. The results are shown in Table 4.

TABLE 4

| Compound | Dosage (a.i. g) per 1 kg of seeds | Sowing method of paddy rice | *Monochoria vaginalis* | *Lindernia procumbens* | Paddy rice |
|---|---|---|---|---|---|
| Pyrazolate | 600 | Surface sowing | 10 | 10 | 0 |

Test Example 5

In 100 cm² of a pot was filled a paddy field soil, and after paddling, seeds of *Lindernia procumbens* and *Scirpus juncoides* Roxb. were sown and mixed into the surface layer of the soil. Paddy rice seeds (variety: Nipponbare) sprouted into a pigeon breast shape were dust-coated with a predetermined amount of wettable powder each prepared according to Preparation examples 3, 4 and 8, and were sown onto the surface of the soil or into the soil (depth: 1 cm) at an amount of 10 grains/pot. After the sowing, water was introduced quietly and flooded up to 1 cm. After 20 days from the sowing, a growth inhibition rate was judged according to the following judgement criteria. The results are shown in Table 5.

TABLE 5

| Compound | Dosage (a.i. g) per 1 kg of seeds | Sowing method of paddy rice | *Lindernia procumbens* | *Scirpus juncoides* Roxb. | Paddy rice |
|---|---|---|---|---|---|
| Sulcotrione | 1.0 | Surface sowing | 10 | 9 | 0 |
| Imazosulfuron | 1.0 | | 10 | 10 | 0 |
| Oxadiargyl | 0.15 | | 10 | 2 | 7 |
| Sulcotrione | 1.0 | Sowing into soil | 10 | 8 | 3 |
| Imazosulfuron | 1.0 | | 10 | 9 | 3 |
| Oxadiargyl | 0.15 | | 10 | 1 | 9 |

Test Example 6

In 100 cm² of a pot was filled a paddy field soil, and after paddling, seeds of *Echinochloa oryzicola* and *Scirpus juncoides* Roxb. were sown and mixed into the surface layer of the soil. Paddy rice seeds (variety: Nipponbare) sprouted into a pigeon breast shape were dust-coated with a predetermined amount of wettable powder each prepared according to Preparation examples 5, 6 and 9, and were sown onto the surface of the soil or into the soil (depth: 1 cm) at an amount of 10 grains/pot. After the sowing, water was introduced quietly and flooded up to 1 cm. After 20 days from the sowing, a growth inhibition rate was judged according to the above-mentioned judgement criteria. The results are shown in Table 6.

TABLE 6

| Compound | Dosage (a.i. g) per 1 kg of seeds | Sowing method of paddy rice | *Echinochloa oryzicola* | *Scirpus juncoides* Roxb. | Paddy rice |
|---|---|---|---|---|---|
| Pyrimisulfan | 0.5 | Surface sowing | 10 | 10 | 1 |
| Pyriminobac-methyl | 1.5 | | 10 | 0 | 0 |
| Butachlor | 1.25 | | 7 | 0 | 5 |
| Pyrimisulfan | 0.5 | Sowing into soil | 8 | 10 | 4 |
| Pyriminobac-methyl | 1.5 | | 10 | 0 | 3 |
| Butachlor | 1.25 | | 5 | 0 | 8 |

Test Example 7

In 100 cm² of a pot was filled a paddy field soil, and after paddling, seeds of *Echinochloa oryzicola* was sown and mixed into the surface layer of the soil. Paddy rice seeds (variety: Nipponbare) sprouted into a pigeon breast shape were dust-coated with a predetermined amount of COMMAND3ME™ (clomazone: 31.4%, available from FMC Corporation), and were sown onto the surface of the soil at an amount of 10 grains/pot. After the sowing, water was introduced quietly and flooded up to 1 cm. After 21 days from the sowing, a growth inhibition rate was judged according to the above-mentioned judgement criteria. The results are shown in Table 7.

TABLE 7

| Compound | Dosage (a.i. g) per 1 kg of seeds | Sowing method of paddy rice | *Echinochloa oryzicola* | Paddy rice |
|---|---|---|---|---|
| Clomazone | 2.5 | Surface sowing | 9 | 1 |

Test Example 8

In 100 cm² of a pot was filled a paddy field soil, and after paddling, seeds of *Monochoria vaginalis* and *Lindernia procumbens* were sown and mixed into the surface layer of the soil. Paddy rice seeds (variety: Nipponbare) sprouted into a pigeon breast shape were dust-coated with predetermined amounts of wettable powder prepared according to Preparation example 1 and TACHIGAREN ® powder formulation (hydroxyisoxazole: 4.0%, available from Mitsui Chemicals Agro, Inc.), and were sown onto the surface of the soil at an amount of 10 grains/pot. After the sowing, water was introduced quietly and flooded up to 1 cm. After 20 days from the sowing, a growth inhibition rate was judged according to the above-mentioned judgement criteria. The results are shown in Table 8.

TABLE 8

| Compound | Dosage (a.i. g) per 1 kg of seeds | Sowing method of paddy rice | Monochoria vaginalis | Lindernia procumbens | Paddy rice |
|---|---|---|---|---|---|
| Pyrazolate + Hydroxyisoxazole | 150 + 1.2 | Surface sowing | 10 | 10 | 0 |

Test Example 9

In 100 cm² of a pot was filled a paddy field soil, and after paddling, seeds of *Monochoria vaginalis* and *Lindernia procumbens* were sown and mixed into the surface layer of the soil. Paddy rice seeds (variety: Nipponbare) sprouted into a pigeon breast shape were dust-coated with a predetermined amount of wettable powder each prepared according to Preparation examples 1 and 10, and were sown onto the surface of the soil at an amount of 10 grains/pot. After the sowing, water was introduced quietly and flooded up to 1 cm. After 20 days from the sowing, a growth inhibition rate was judged according to the above-mentioned judgement criteria. The results are shown in Table 9.

TABLE 9

| Compound | Dosage (a.i. g) per 1 kg of seeds | Sowing method of paddy rice | Monochoria vaginalis | Lindernia procumbens | Paddy rice |
|---|---|---|---|---|---|
| Pyrazolate + Dinotefuran | 150 + 5 | Surface sowing | 10 | 10 | 0 |

Test Example 10

In 100 cm² of a pot was filled a paddy field soil, and after paddling, seeds of *Monochoria vaginalis* and *Lindernia procumbens* were sown and mixed into the surface layer of the soil. Paddy rice seeds (variety: Nipponbare) sprouted into a pigeon breast shape were dust-coated with a predetermined amount of wettable powder each prepared according to Preparation examples 5 and 11, and were sown onto the surface of the soil at an amount of 10 grains/pot. After the sowing, water was introduced quietly and flooded up to 1 cm. After 20 days from the sowing, a growth inhibition rate was judged according to the above-mentioned judgement criteria. The results are shown in Table 10.

TABLE 10

| Compound | Dosage (a.i. g) per 1 kg of seeds | Sowing method of paddy rice | Monochoria vaginalis | Lindernia procumbens | Paddy rice |
|---|---|---|---|---|---|
| Pyrimisulfan + Dymron | 1 + 40 | Surface sowing | 10 | 10 | 0 |
| Pyrimisulfan | 1 | | 10 | 10 | 3 |

As can be clearly seen from Test examples 1 to 10, control of weeds can be accomplished by sowing the paddy rice seeds of the present invention onto the surface of the soil of the paddy field. In addition, as compared with the various kinds of the weeds tested, a degree of inhibiting growth of the paddy rice was markedly low, whereby high safety to the paddy rice could be shown.

UTILIZABILITY IN INDUSTRY

The paddy rice seed and the method for controlling weed of the present inventions, which can be used for the paddy rice cultivation, control principal weeds and yet cause no chemical damage against the paddy rice with accomplishing labor-saving of spreading the herbicide, and thus are excellent inventions.

The invention claimed is:

1. A paddy rice seed coated by iron powder and/or calcium peroxide and treated by a herbicidal composition comprising, as an active ingredient(s)
   (A1) a bleaching herbicidal compound selected from the group consisting of a pyrazole compound, a triketone compound and 6-chloro-3-(2-cyclopropyl-6-methylphenoxy)pyridazin-4-yl-morpholin-4-carboxylate and/or
   (A2) a herbicidal compound of acetolactate synthase inhibitor selected from the group consisting of sulfonylurea and pyrimidinyl salicylic acid and a salt thereof.

2. The paddy rice seed according to claim 1, wherein the bleaching herbicidal compound is pyrazolate and/or 6-chloro-3-(2-cyclopropyl-6-methylphenoxy)pyridazin-4-ylmorpholin-4-carboxylate.

3. The paddy rice seed according to claim 2, wherein the bleaching herbicidal compound is pyrazolate.

4. The paddy rice seed according to claim 1, wherein the herbicidal compound of acetolactate synthase inhibitor is sulfonylurea and/or pyrimidinyl salicylic acid.

5. The paddy rice seed according to claim 1, wherein the herbicidal compound of acetolactate synthase inhibitor is azimsulfuron, bensulfuron-methyl, cyclosulfamuron, halosulfuron-methyl, ethoxysulfuron, imazosulfuron, pyrazosulfuron-ethyl, chlorimuron-ethyl, cinosulfuron, metsulfuron-methyl, flucetosulfuron, propylsulfuron or metazosulfuron.

6. The paddy rice seed according to claim 1, wherein the herbicidal compound of acetolactate synthase inhibitor is bispyribac, pyribenzoxim, pyriftalid, pyriminobac-methyl, pyrimisulfan or triafamone.

7. The paddy rice seed according to claim 1, wherein the seed is coated by iron powder and treated by the herbicidal composition.

8. The paddy rice seed according to claim 1, wherein the seed is coated by iron powder and calcium peroxide and treated by the herbicidal composition.

9. The paddy rice seed according to claim 1, wherein an amount of an active ingredient of the herbicidal composition to be formulated based on 1 kg of the paddy rice seed is 0.01 g to 3,000 g.

10. The paddy rice seed according to claim 1, wherein an amount of an active ingredient of the herbicidal composition to be formulated based on 1 kg of the paddy rice seed is 0.1 g to 1,000 g.

11. A method for controlling weed which comprises sowing a paddy rice seed coated by iron powder and/or calcium peroxide and treated by a herbicidal composition which comprises, as an active ingredient(s),
(A1) a bleaching herbicidal compound selected from the group consisting of a pyrazole compound, a triketone compound and 6-chloro-3-(2-cyclopropyl-6-methylphenoxy)pyridazin-4-yl morpholin-4-carboxylate and/or
(A2) a herbicidal compound of acetolactate synthase inhibitor selected from the group consisting of sulfonylurea, pyrimidinyl salicylic acid synthase and a salt thereof on a surface of a soil of a paddy field.

12. The method for controlling weed according to claim 11, wherein the bleaching herbicidal compound is pyrazolate and/or 6-chloro-3-(2-cyclopropyl -6-methylphenoxy) pyridazin-4-yl morpholin-4-carboxylate.

13. The method for controlling weed according to claim 11, wherein the bleaching herbicidal compound is pyrazolate.

14. The method for controlling weed according to claim 11, wherein the herbicidal compound of acetolactate synthase inhibitor is sulfonylurea and/or pyrimidinyl salicylic acid.

15. The method for controlling weed according to claim 11, wherein the herbicidal compound of acetolactate synthase inhibitor is azimsulfuron, bensulfuron-methyl, cyclosulfamuron, halosulfuron-methyl, ethoxysulfuron, imazosulfuron, pyrazosulfuron-ethyl, chlorimuron-ethyl, cinosulfuron, metsulfuron-methyl, flucetosulfuron, propylsulfuron or metazosulfuron.

16. The method for controlling weed according to claim 11, wherein the herbicidal compound of acetolactate synthase inhibitor is bispyribac, pyribenzoxim, pyriftalid, pyriminobac-methyl, pyrimisulfan or triafamone.

17. The method for controlling weed according to claim 11, wherein an amount of an active ingredient of the herbicidal composition to be formulated based on 1 kg of the paddy rice seed is 0.01 g to 3,000 g.

18. The method for controlling weed according to claim 11, wherein an amount of an active ingredient of the herbicidal composition to be formulated based on 1 kg of the paddy rice seed is 0.1 g to 1,000 g.

* * * * *